(12) United States Patent
Peck et al.

(10) Patent No.: US 8,617,553 B2
(45) Date of Patent: Dec. 31, 2013

(54) USE OF GOAT SERUM FOR VETERINARY TREATMENT

(75) Inventors: Graham Joseph Peck, Shoreham (GB); Juliette Peck, Shoreham (GB)

(73) Assignee: Aimsco Limited, East Sussex (GB)

( * ) Notice: Subject to any disclaimer, the term of this patent is extended or adjusted under 35 U.S.C. 154(b) by 0 days.

(21) Appl. No.: 13/562,863

(22) Filed: Jul. 31, 2012

(65) Prior Publication Data

US 2012/0294951 A1 Nov. 22, 2012

Related U.S. Application Data

(60) Continuation of application No. 13/134,512, filed on Jun. 9, 2011, now abandoned, which is a continuation of application No. 12/384,681, filed on Apr. 9, 2009, now abandoned, which is a division of application No. 10/582,452, filed as application No. PCT/GB2004/050040 on Dec. 10, 2004, now abandoned.

(30) Foreign Application Priority Data

| Dec. 11, 2003 | (GB) | 0328650.7 |
| Mar. 1, 2004 | (GB) | 0404533.2 |
| Mar. 1, 2004 | (GB) | 0404534.0 |

(51) Int. Cl.
*A61K 39/42* (2006.01)
*A61K 39/395* (2006.01)

(52) U.S. Cl.
USPC .................. 424/148.1; 424/147.1; 424/130.1

(58) Field of Classification Search
None
See application file for complete search history.

(56) References Cited

FOREIGN PATENT DOCUMENTS

WO  03064472 A2  8/2003

OTHER PUBLICATIONS

The Merck Manuals Online Medical Library, [online]. Whitehouse Station, NJ: Merck Research Laboratories, 2006-2007. [retrieved on Feb. 15, 2013]. Retrieved from the Internet: < URL: http://www.merckmanuals.com/vet/print/respiratory_system/respiratory_diseases_of_horses/recurrent_airway_obstruction_in_horses.html>. Recurrent Airway Obstruction in Hor.*
Chen et al., "The value of the lipopolysaccharide-induced acute lung injury model in respiratory medicine," Expert Review of Respiratory Medicine, vol. 4, No. 6, Dec. 2010, p. 773.
Martin et al., "Experimental Models and Emerging Hypotheses for Acute Lung Injury," Crit Care Clin., Jul. 2011, pp. 735-752.
Mirzapoiazova et al., "Supression of endotoxin-induced inflammation by taxol," European Respiratory Journal, vol. 30, No. 3, 2007, pp. 429-435.

* cited by examiner

*Primary Examiner* — Sharon Wen
(74) *Attorney, Agent, or Firm* — Merchant & Gould; Gary M. Myles

(57) ABSTRACT

Methods for veterinary treatment of mammals are described, for treatment of conditions having an inflammatory component. The methods are particularly suited to treatment of cats, dogs, or horses.

4 Claims, No Drawings

USE OF GOAT SERUM FOR VETERINARY TREATMENT

This application is a continuation application of application Ser. No. 13/134,512, filed Jun. 9, 2011 now abandoned, which is a continuation application of application Ser. No. 12/384,681, filed Apr. 9, 2009 now abandoned, which is a divisional application of application Ser. No. 10/582,452, filed Mar. 28, 2007, abandoned, which is the national phase application of PCT Application No. PCT/GB2004/050040, filed Dec. 10, 2004, which claims priority based on United Kingdom Patent Application No. 0404533.2, filed Mar. 1, 2004, United Kingdom Patent Application No. 0404534.0, filed Mar. 1, 2004, and United Kingdom Patent Application No. 0328650.7, filed Dec. 11, 2003, the contents of which are incorporated by reference in their entireties.

FIELD OF THE INVENTION

The present invention relates to a method of veterinary treatment of animals; in particular, but not exclusively, aspects of the invention relate to methods of treatment of various inflammatory diseases, or diseases with an inflammatory component, in canines and felines. Other aspects of the invention relate to treatment of further diseases in canines and felines, while a yet further aspect of the invention relates to a method of treatment of equine chronic obstructive pulmonary disease. Certain aspects of the invention relate to a medicament for treatment of such diseases.

BACKGROUND OF THE INVENTION

PCT publications WO 03/004049 and WO 03/064472 describe therapeutic agents and treatments which are based on a serum composition with many surprising beneficial effects. The respective content of each of these two texts is incorporated in full by specific reference. In particular, the reader is referred to them for an understanding of how the therapeutic agent can be prepared, and for the indications which can be treated. Typically a goat is immunised with HIV-3B viral lysate raised in H9 cells. The resulting serum is believed to be active against HIV, and multiple sclerosis. The reader is further referred in particular to the section on pages 3 and 4 of WO03/004049 headed 'Example of Production of Goat Serum' for further details of the production of serum. This section is incorporated herein by reference.

In addition to the uses described in the earlier PCT publications, it has been surprisingly identified that the serum composition may be active against a variety of veterinary conditions, among them canine atopic dermatitis, canine oral melanoma, and equine COPD, as well as other canine and feline diseases having an inflammatory component.

Canine atopic dermatitis is a common problem affecting around 15% of dogs, with the principal symptom being pruritus (itching) initially round the face, axilla, front legs and later over the trunk.

Canine atopic dermatitis is generally caused by an allergic response to allergens such as pollens, grasses, dust mites and moulds. Secondary skin infections may also develop, leading to great discomfort for the animal.

Current therapies generally take a number of approaches:
1. The allergic reaction may be blocked, by anti-inflammatory therapy. Steroids can be given orally or by injection and may be combined with antihistamines and fatty acid supplements.
2. Relief from itching may be given by use of topical agents.
3. The allergic reaction may be reduced by means of hyposensitisation. Once specific allergy sources are identified, small amounts of the antigens are injected regularly to desensitise the animal. Injections usually need to be continued for a significant length of time, with the treatment being relatively expensive. Further, success rates are limited.
4. Cyclosporins may be used as a treatment for atopic dermatitis.

There is a need for an alternative treatment for canine atopic dermatitis.

Oral malignant melanomas comprise about 30-40% of all malignant oral tumours in dogs, and occur most frequently in older, smaller, male dogs. Common signs of oral melanoma are drooling (sometimes with bloody saliva), decreased eating, and halitosis (bad breath). Other signs may include coughing, difficulties in swallowing, and weight loss. Some breeds also suffer from a vigorous development of tumour masses on their gums and around the teeth, which can pose physical problems during eating.

Tumours smaller than 1 centimetre in size offer the best prognosis, because larger melanomas often metastasize in the early stages to the regional lymph nodes, lungs, and other organs. If the dog is already has metastases at the time of diagnosis, the disease is advanced, and the prognosis is poor.

Current treatment of canine oral melanoma tends to rely on surgical excision and radiation. Because complete excision of the cancer is often difficult and tumour recurrence is common, the prognosis even after surgical excision is poor. The median survival time for dogs with oral melanoma is 8 months after diagnosis. Adjuvant therapies such as chemotherapy, immunotherapy, and experimental gene therapy are often applied because of the cancer's high rate of metastasis.

There is a need for an alternative treatment for canine oral melanoma.

Equine chronic obstructive pulmonary disease (COPD), also known as heaves or broken wind, is a respiratory disorder of horses. COPD is caused by inflammation of airways in response to particular allergens, and may result in difficult breathing, nasal discharge, exercise intolerance, and anxiety in the affected animal. In certain cases, secondary bacterial infections may also occur.

Incidence of COPD in horses in parts of northern Europe is believed to be as high as 50%, while a lower, but still common, incidence rate is reported from the northern United States. Besides being frequent, equine COPD may eventually lead to decreased performance capacity, to early retirement from sporting activity, and ultimately to euthanasia.

Typical allergens responsible for COPD include dust, moulds, hay, straw, pollens, and the like. The preferred treatment for COPD is to isolate the affected animal from the allergens; however, it will be appreciated that this may not always be possible. An alternative, or additional, treatment may be administration of antihistamines, steroids, and bronchodilators to reduce the severity of attacks.

There is a need for an alternative treatment for COPD.

SUMMARY OF THE INVENTION

According to a first aspect of the present invention, there is provided a method of veterinary treatment of a mammal, the method comprising administering a serum composition obtained from a goat after challenge with an immunogen.

The invention also provides a method of veterinary treatment of a mammal, the method comprising administering a serum composition obtainable from a goat after challenge with an immunogen.

Also provided is the use of a serum composition obtained from a goat after challenge with an immunogen in the manufacture of a medicament for the veterinary treatment of a mammal; and the use of a serum composition obtainable from a goat after challenge with an immunogen in the manufacture of a medicament for the veterinary treatment of a mammal.

Also provided is a pharmaceutical composition for the veterinary treatment of a mammal, the composition comprising a serum composition obtained from a goat after challenge with an immunogen, suitable for administration to a subject mammal.

The mammal is preferably a canine, a feline, or an equine. More preferably the mammal is a dog, a cat, or a horse.

The treatment may be for a disorder having an inflammatory component, and may be selected from arthritis or other joint disease; inflammatory gastrointestinal disease, including pancreatitis and hepatitis/cholangiohepatitis/cholangitis, preferably in canines and felines; urinary tract inflammation in canines and felines, including cystitis and interstitial cystitis; allergic skin disease in canines and felines, including dermatitis, atopy in canines, canine atopic dermatitis, and eosinophilic inflammatory disease in felines; inflammatory respiratory disease, including canine bronchitis, chronic airway disease, fibrosing alveolitis, feline asthma, and equine respiratory disorders including chronic obstructive pulmonary disease; and gingivitis and stomatitis in felines.

Other disorders which may be treated include renal failure in canines and felines; wound healing in mammals; and prostatic disease in canines. Other skin disorders in canines and felines may also be treated. The method and composition may also be useful in treatment of neurological disorders or spinal injury in mammals. The invention may also be used to treat cancers, in particular melanomas, especially oral melanoma, and particularly canine oral melanoma.

The immunogen may comprise HIV. This may be presented in intact host cells, in cell-free extracts, as a viral lysate, or in a mixture thereof.

Alternatively, in a variation of the invention, following heat inactivation of a supernate solution upon which a viral culture has been grown or which is capable of the same, but has not been used to grow a culture, may also be used as an immunogen which will produce a suitable response. Any supernate solution or other medium which is suitable for the in vitro growth of HIV or another virus may be used to produce an acceptable immunogen, which will produce an effective response. The supernate of a cell culture growth medium such as PMBC or the cancer immortal cell line as used to grow HIV 3b are given as an example. The HIV or other selected virus does not need to be present to produce an effective immunogen to create the composition.

Other suitable immunogens are recited on pages 12 and 13 of WO03/064472, the contents of which are incorporated herein by reference.

An example of preparation of goat serum is given below.

The serum composition is preferably administered in a dosage of between 0.01 and 10 mg/kg to the subject; more preferably between 0.01 and 5 mg/kg, between 0.05 and 2 mg/kg, and most preferably between 0.1 and 1 mg/kg. The precise dosage to be administered may be varied depending on such factors as the species, age, sex, and weight of animal, the method and formulation of administration, as well as the nature and the severity of the condition to be treated. For example, in treatment of COPD in equines, preferred dosage ranges are between 1 and 20 mg of composition to the equine; more preferably between 4 and 15 mg, and most preferably between 6 and 10 mg. Other factors such as diet, time of administration, condition of the animal, drug combinations, and reaction sensitivity may be taken into account.

The serum composition may be administered by any effective route, preferably by subcutaneous injection, although alternative routes which may be used include intramuscular or intralesional injection, oral, aerosol, parenteral, or topical. Examples of pharmaceutical compositions include any solid (tablets, pills, capsules, granules, ointments, etc) with suitable composition for oral, topical, or parenteral administration; fluids suitable for injection; or aerosols suitable for administration to an animal. The compositions may include a carrier.

An effective treatment regimen may be determined by the clinician or veterinarian responsible for the treatment, and may depend on factors such as the species, age, sex, and weight of the animal, the method of administration, and the nature and severity of the disorder to be treated. Other factors such as diet, time of administration, condition of the animal, drug combinations, and reaction sensitivity may be taken into account. One preferred regimen is the subcutaneous injection of between 0.1 and 0.5 mg/kg of serum composition in a liquid formulation. A single dose is thought to offer an improvement in the condition of the animal for some 2 to 5 days. This is the preferred regimen for treatment of canine atopic dermatitis, and canine oral melanoma. An alternative treatment regimen, which may be suitable for more severe conditions, is the administration of 1 mg/kg serum composition by subcutaneous injection once daily for one week. Injections may need to be repeated at weekly to monthly intervals indefinitely in order to control the condition.

The serum composition may, but need not, comprise anti-HLA antibody. It is believed that this may play a role in the activity of the serum.

According to a further aspect of the present invention, there is provided a method of veterinary treatment of a mammal, the method comprising administering a serum composition comprising anti-HLA antibody. It is believed that at least a component of the serum activity is linked with anti-HLA activity; the activity may reside in the antibody itself or in some other factor associated with the antibody. Preferably the anti-HLA antibody is goat anti-HLA antibody. The antibody may be polyclonal.

DETAILED DESCRIPTION OF THE INVENTION

Example of Production of Goat Serum

A goat was inoculated by intramuscular injection with lysed HIV viral cocktail and formulated with Freunds adjuvant. The virus was previously heat killed at 60° C. for 30 minutes. Blood samples were drawn after an appropriate interval, such as two weeks, for initial assessment. In the optimised procedure, the goat is injected every week for four weeks, then at six weeks the animal is bled to obtain the reagent.

Approximately 400 cc of blood is drawn from the goat under sterile technique. The area for needle extraction is shaved and prepared with betadine. An 18-gage needle is used to draw approximately 400 cc of blood from the animal. Of note is that the animal can tolerate approximately 400 cc of blood drawn without the animal suffering any untoward effects, The animal does not have to be sacrificed. The animal can then be re-bled in approximately 10 to 14 days after it replenishes its blood volume.

The presence of potentially useful antibodies was confirmed, having regard to the desired antibody activity. Once the presence of such reagents was confirmed, blood was then taken from the goat at between 4-6 weeks.

The base blood product in order to create the reagent is then centrifuged to create the serum, 300 ml of serum was then filtered to remove large clots and particulate matter. The serum was then treated with supersaturated ammonium sulphate (45% solution to room temperature), to precipitate antibodies and other material. The resulting solution was centrifuged at 5000 rpm for five minutes, after which the supernatant fluid was removed. The precipitated immunoglobulin was resuspended in phosphate-buffered saline (PBS buffer, see Sambrook et al, 'Molecular Cloning: A Laboratory Manual', 1989) sufficient to redissolve the precipitate.

The solution was then dialysed through a membrane with a molecular weight cut off of 10,000 Daltons. Dialysis was carried out in PBS buffer, changed every four hours over a period of 24 hours. Dialysis was carried out at 4° C.

After 24 hours of dialysis the contents of the dialysis bag were emptied into a sterile beaker. The solution was adjusted such that the mass per unit volume =10 mg per ml. The dilution was carried out using PBS. The resulting solution was then filtered through a 0.2 micron filter into a sterile container, After filtration, the solution was aliquoted into single dosages of 1 ml and stored at −22° C. prior to use.

Administration of Serum

A 1 ml aliquot of serum, prepared as described, is injected intramuscularly to a mammalian subject. The treatment is repeated daily for seven days.

Experimental Results

Domestic pets (canines and felines) have been treated with the serum at doses ranging from 0.04 to 1.3 mg/kg (dogs), and from 0.14 to 1.2 mg/kg (cats). No significant side effects have been reported. Summaries of the treatments are as follows.

Conditions Treated

1. Arthropathy and Musculoskeletal Problems

Twelve dogs treated as primary complaint, four other dogs had as a secondary problem. Five animals have been reported as significantly improved, five have shown no response (including three treated for other problems), and two were ambiguous. One animal was withdrawn by owner, and one the owner reports no longer has bad days.

2. Gastro-Intestinal Problems Including Pancreatitis

Five animals treated as primary complaint, three others as secondary problem. Six animals reported as significantly improved or condition resolved (including two treated for other problems). One animal with pancreatitis enormously improved in demeanour after a single injection, but continued to vomit.

3. Skin Disease

Five animals treated as primary complaint, two others as secondary problem. Five reported as significantly improved including the two treated for other problems.

Case Studies

Four domestic dogs were treated with the serum. Summaries of their conditions and responses are as follows.

Summary for Patient 1.

Primary condition for treatment: Chronic lick lesions over both carpii and right pes apparently associated with degenerative joint disease.

Concurrent active conditions and treatments: Polyarthropathy with bilateral carpal varus due to degenerative joint disease.

Apparent response to Treatment: After two injections owner left lick lesion uncovered and dog has not licked at since.

Adverse reactions: None reported.

Summary for Patient 2:

Primary condition for treatment: Atopy and interdigital cysts—evening primrose oil Concurrent active conditions and treatments: Multiple generalised sebaceous cysts that dog chews at. Inflammatory bowel disease—dietary management and protexin. Occasional injection of dexadreson to manage acute flare up. However extended steroid treatment (inhaled or tablet) results in marked side effects. Chronic allergic respiratory disease—responds to antihistamine and inhaled steroids Apparent response to Treatment: Over the course of one months treatment with serum noticeable improvement in condition of skin and coat. Decreased inflammation associated with generalised sebaceous cysts. Since treatment no episodes of inflammatory bowel disease has occurred. On stopping antihistamine the respiratory signs recurred despite treatment.

Adverse reactions: Increased appetite reported.

Summary for Patient 3:

Primary condition for treatment: Progressive alopecia with borderline low thyroid levels (awaiting skin biopsy results).

Concurrent active conditions and treatments: Upper respiratory noise especially when excited, no evidence of collapsing trachea.

Apparent response to Treatment: Only one injection so far.

Adverse reactions: None reported.

Summary for Patient 4

Primary condition for treatment: Atopy

Concurrent active conditions and treatments: Persistently elevated ALT and ALKP but despite investigation no cause of this has been identified.

Apparent response to Treatment: Only one injection so far.

Adverse reactions: After first injection on returning home, owner reports hyperexcitable and running around house.

The invention claimed is:

1. A method of veterinary treatment of a mammal for an inflammatory respiratory disease, comprising administering a serum composition obtained from a goat after challenge with HIV, wherein the inflammatory respiratory disease is selected from the group consisting of chronic obstructive pulmonary disease, chronic airway disease, and equine respiratory disorders.

2. The method of claim 1 wherein the mammal is an equine.

3. The method of claim 1 wherein the disease is chronic obstructive pulmonary disease.

4. The method of claim 1 wherein the disease is chronic airway disease.

* * * * *